United States Patent [19]

Nagakura

[11] Patent Number: 5,120,728
[45] Date of Patent: Jun. 9, 1992

[54] CEPHALOSPORIN COMPOUNDS

[75] Inventor: Isao Nagakura, Aichi, Japan

[73] Assignee: Pfizer Inc., New York, N.Y.

[21] Appl. No.: 583,412

[22] Filed: Sep. 17, 1990

[30] Foreign Application Priority Data

Sep. 29, 1989 [JP] Japan .................................. 1-254331

[51] Int. Cl.$^5$ .................. C07D 501/24; A61K 31/545
[52] U.S. Cl. ..................................... 514/202; 540/222
[58] Field of Search ................ 514/201, 202; 540/222, 540/221

[56] References Cited

FOREIGN PATENT DOCUMENTS 269298  6/1988  European Pat. Off. .
295341  12/1988 European Pat. Off. .
62-51688  3/1987  Japan .
62-209082 9/1987  Japan .

Primary Examiner—Nicholas S. Rizzo
Attorney, Agent, or Firm—Peter C. Richardson; J. Trevor Lumb; A. Dean Olson

[57] ABSTRACT

Certain cephalosporin compounds, and their pharmaceutically- accepted salts or in vivo hydrolyzable esters are useful as antibacterial agents.

10 Claims, No Drawings

CEPHALOSPORIN COMPOUNDS

TECHNICAL FIELD

This invention relates to a new series of cephalosporin compounds which are of value as antibacterial agents. More particularly, it is concerned with novel 3-cephem compounds (delta-3-cephem compounds) having a 2-(2-aminothiazol-4-yl)-2-(substituted hydroxyimino)acetamido group at the 7-position.

BACKGROUND OF THE INVENTION

The cephalosporins are a well-known family of antibiotics that have gained wide-spread use in recent years in the treatment of pathogenic infections in mammals. A large number of cephalosporins have been prepared by varying the substituents at the 3- and 7-positions of the cephalosporin nucleus. However, the search still continues for compounds having high activity and a high degree of stability.

Although some newly-discovered cephalosporins have proven to be invaluable by virtue of their broad antibacterial spectrum against Gram-positive and Gram-negative bacteria, they do not appear to be effective against certain bacteria, e.g., *Klebsiella pneumoniae*, *Proteus mirabillisci*, *Proteus vulgaris*, *Proteus morganii*, and particularly *Pseudomonas aeruginosa*. These are noted as pathogens which cause serious infections in hospitals and clinics. One of the successful antibiotics against the above-mentioned bacteria is cephem having catechol moiety in 3-position. Japanese patent SHO-62-51688, SHO-62-148489, SHO-62-209082 and EP0269-298 disclose a cephalosporin compound of the formula

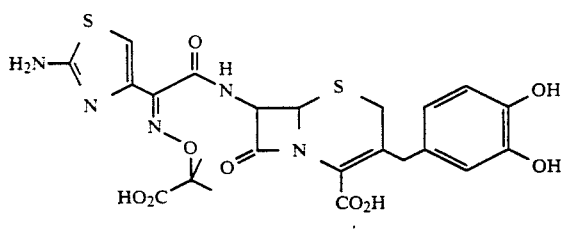

This compound presents extremely high activity on MIC against gram negative bacteria, particularly against ps. aureginosa. However in vivo activity is lessened due to deactivation by COMT (catechol O-methyl transferase). During intensive study to circumvent the COMT-deactivation we found that the cephems having catechol substituted with halogen and/or nitro are resistent against COMT.

SUMMARY OF THE INVENTION

The novel 3-cephem compounds of the present invention are represented by the following structural formula:

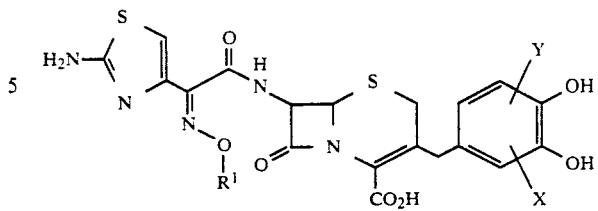

"wherein $R^1$ is lower alkyl substituted by a carboxyl, cyano, halo, hydroxyl or protected carboxyl group; and (A) X is hydrogen or halo and Y is halo, or (B) X is hydrogen and Y is nitro,"

or a pharmaceutically-acceptable salt or in vivo hydrolysable ester thereof. The term "lower alkyl" is intended to encompass an alkyl having up to 6 carbon atoms, preferably up to 4 carbon atoms, and, where appropriate, such a group may be straight or branched chain.

The term "halo" means fluoro, chloro, bromo or iodo.

The term "protected carboxyl group" means a COOH group protected by those groups commonly employed to protect a carboxyl group such as benzyl, benzhydryl, p-nitrobenzyl, t-butyl etc.

"Pharmaceutically-acceptable salt" refers to either an acid-addition salt or a cationic salt. The former includes, but is not limited to phosphoric acid, citric acid, p-toluenesulfonic acid, 2-naphthalenesulfonic acid and methanesulfonic acid salts, and the like. The latter includes, but is not limited to, sodium, potassium, calcium N,N'-dibenzylethylenediamine, triethylamine and procaine salts, and the like.

The term "in vivo hydrolysable ester" refers to esters which are hydrolysable under physiological conditions such as acetoxymethyl, pivaloyloxymethyl, 1-(ethoxycarbonyloxy) ethyl, 3-phthalidyl, gammabutyrolacton-4-yl and 5-methl-2-oxo-1,3-dioxol-4-yl-methyl ester. Such esters are generally used to enhance oral absorption and are well-documented in the penicillin and cephalosporin art.

The group $R^1$ is a group of $C_1$-$C_6$ alkyl being substituted by carboxyl, cyano or fluoro. The preferred $R^1$ is a group of $C_1$-$C_6$ alkyl being substituted by carboxyl, cyano or fluoro. The preferred $R^1$ groups are of the formula: $CH_3$, $-CH_2-COOH$, $-CH_2-CH_2-F$, $-CH_2-CN$ and $-C(CH_3)_2-COOH$.

Examplary X and Y are hydrogen, fluoro, chloro, bromo or iodo or nitro in the position of 2,5-dihalo, 2,6-dihalo or 5,6-dihalo having the same halo group or a different halo group. When one of X or Y is hydrogen, the position of halo or nitro group may be one of the selected positions of 2 or 5.

Preferred examples of the compounds of formula (II) are: 7-(2-(2-aminothiazol-4-yl)-2-syn-(1-carboxy-1-methylethoxyimino)acetamido) -3-(2,5-difluoro-3,4-dihydroxypenyl)methyl-3-cephem-4-carboxylic acid; 7-(2-(2-aminothiazol-4-yl)-2-syn-(1-carboxyl-1-methylethoxyimino)-acetamido) -3-(2,5-dichloro-3,4-dihydroxyphenyl)methyl-3-cephem-4-carboxylic acid; and 7-(2-(2-aminothiazol 4-yl)-2-syn-(1-carboxy-1-methylethoxyimino)acetamido) -3- (2,6-dibromo-3,4-dihydroxyphenyl) methyl-3-cephem-4-carboxylic acid.

It is to be noted that due to the presence of the iminoether moiety in compound (II), geometrical isomers may exist. Although only the syn isomer form is depicted in the structural formula (II) and this is preferred, the anti isomer is also possible. Both isomers and mixtures thereof are included within the scope of the present invention.

Also encompassed by the present invention is a pharmaceutical composition comprising of formula (II) and a pharmaceutically acceptable diluent or carrier; and a method of treating a bacterial infection in a mammal (especially a human) which comprises administering an antibacterially effective amount of a compound of formula (II) to said mammal.

DETAILED DESCRIPTION OF THE INVENTION

The novel cephalosporin compounds of the present invention may be prepared by acylating 7-amino-3-substituted cephalosporins with an appropriately-protected acylating agent and then removing the protecting group when present.

A typical route to the compounds of formula (II) is outlined below:

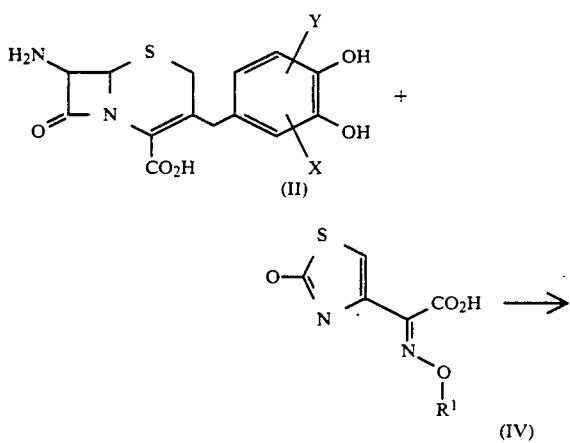

In the above formulae, $R^1$, X and Y are as herein-before defined and Q is amino or a protected amino group. The starting material can be prepared, e.g., by the methods described in Japanese Patent Appln. 59-160-998 (Kokai No. 61-37,788, published Feb. 22, 1986) by reacting 7-amino-cephalosporanic acid with an appropriate displacing agent (i.e., AH) in the presence of a Lewis acid.

The carboxylic acid group of the acylating agent is activated by any of the standard methods such as conversion to the mixed anhydride, acid chloridie, acid imidazolide or activated ester. A preferred activated derivative is an active ester, e.g., benzothiazole thioester, p-nitrophenylster, N-methyl tetrazole thioester, N-hydroxysuccinimide ester or N-hydroxybenzotriazole ester.

The acylation reaction is typicaly carried out using an active ester or the acid at $-20° \sim 50°$ C. in an organic solvent, e.g., N,N-dimethyl acetamide. Other solvents which can be employed in this reaction include N,N-dimethylformamide, N-methyl-2-pyrrolidone, acetone, methyl ethyl ketone, methyl isobutyl ketone, tetrahydrofuran, dioxane, ethyl acetate, dichloromethane, chloroform, diethylether, water, etc.

For each one mole of the starting material, it is necessary to use at least one equivalent of the acylating agent, preferably 1.0 to 1.2 equivalents. Base, e.g., triethylamine, may also be used in this reaction. Other bases which can be employed in this reaction include pyridine, diisopropyl ethylamine, N-methylmorpholine etc. Reaction temperature is not critical, but it is preferably in the range of $-0°$ C. to $30°$ C.

Any protecting group, if present may be removed after acylation. For example, when Q is formamido, the protecting group can be removed simply by exposure to a small amount of strong, aqueous acid such as hydrochloric acid. When $R^1$ contains tert-butyl, this can be removed by treating with trifluoroacetic acid or formic acid. Finally, the desired cephalosporins can be purified by conventional methods for cephalosporin compounds, e.g., recrystallization or chromatography.

The in vivo hydrolysable esters of the compounds of the formula II can be prepared by conventional methods. They can be prepared directly from a carboxylic acid of the formula II, by conversion into a carboxylate salt (e.g., the sodium salt) followed by alkylation with the appropriate alkyl halide (e.g., iodomethyl pivalate). Alternatively, an in vivo hydrolysable ester of a compound of the formula II can be prepared by acylation of an in vivo hydrolysable ester of a compound of the formula III with a compound of the formula IV.

The pharmaceutically-acceptable cationic salts of the compounds of the present invention are readily prepared by standard methods. For example, one equivalent of the corresponding cationic hydroxide, carbonate or bicarbonate is combined with the carboxylic acid in an organic or aqueous solvent. Of particular value is the sodium salt. In like manner, the pharmaceutically-acceptable acid addition salts are also prepared by standard methods. If these salts precipitate, they are recovered by filtration. Alternatively, they can be recovered by evaporation of the solvent, or, in the case of aqueous solutions, by lypohilization.

The in vivo hydrolysable esters of the compounds of the present invention are readily hydrolysable upon exposure in mammalin blood or tissue, to afford the corresponding cephalosporins. They are believed to improve the absorption characteristics of cephalosporins. Thus these esters are also considered as objects of the present invention.

The utility of the compounds of formula (II) and their pharmaceutically acceptable salts and in vivo hydrolysable esters will be evident from their antib, cterial activity. They are active against both Gram-positive and Gram-negative organisms, particularly against Gram-negative organisms such as *Escherichia coli, Kelebsiella peneumoniae, Proteus vulgaris, Enterobacter cloacae, Serratia marcescens* and *Pseudomonas aeruginosa*. Minimum inhibitory concentrations (MIC's) are measured according to the well-known disc-plate method, using testing ranges from 0.1 to 100 mcg/ml.

The compound of the present invention can be administered orally or parenterally, i.e., intramuscularly, subcutaneously, intraperitoneally or intravenously. For these purposes, the compounds of the invention are normally combined with a pharmaceutically acceptable carrier, according to standard pharmaceutical practice. For oral administration, the compounds can be used in the form of tablets, capsules, lozenges, troches, powders, syrups, elixirs, aqueous solutions and suspensions, and the like. For parenteral administration, sterile solutions are usually used.

In a pharmaceutical composition containing a cephalosporin antibacterial agent of the invention, the weight ratio of the compound of the invention to the pharmaceutically acceptable carrier will be in the range from 4:1 to 1:2.

The daily dosages to be used will not differ significantly form other clinically used cephalosporins. The prescribing physician will ultimately determine the appropriate dose for the given human subject, and this can be expected to vary according to the age, weight, and response of the individual patient as well as the nature and the severity of the patient's symptoms. The compounds of the present invention will normally be used orally at dosages in the range from 20 to about 200 mg per kilogram of body weight per day, and parenterally at dosages from about 10 to about 100 mg per kilogram of body weight per day, usually in divided doses. In some instances it may be necessary to use doses outside these ranges.

The following examples illustrate the invention but are not to be construed as limiting the scope thereof.

Nuclear magnetic resonance spectra (NMR) were measured at 270 MHz for solutions in perdeuterodimethyl sulfoxide (DMSO-$d_6$), and peak positions are expressed in parts per million (ppm) downfield from TMS. The following abbreviations for peak shapes are used: s, singlet, bs, broad singlet, d, doublet; t, triplet; q, quarter; m, multiplet.

EXAMPLE 1

7-Amino-3-(2,5-dichloro-3,4-dihydroxyphenyl)-methyl-3-cephem-4-carboxylic acid.

3.6-dichlorocatechol (5.0 g) was dissolved in a mixture of trifluoroacetic acid (4.3 m)) and dichloromethane (5 ml), then 7-amino-3-cephem-4-carboxylic acid (5.0 g) was dissolved in this mixture. After stirring at 0°~5° C. for 30 minutes boron trifluoride ethyl ether (11.1 ml) was added to the resulting solution and stirred at room temperature for 10 hours.

The resulting solids were filtered off and dried in vacuo. The solids were put into water (30 ml) and dissolved by adjusting the pH to 6.8 with sodium bicarbonate. This solution was washed with ethylacetate, treated with carbon and adjusted the pH to 2.8 with 6N HCl. The resulting solids were filtered off, washed with water and dried in vacuo to give the title compound (3.3 g): NMR (DMSO-$d_6$) 3.08 and 3.30 (AB, J=17Hz, 2H), 3.90 and 4.04 (AB, J=15Hz 2H), 4.08 (d. J=4Hz, 1H), 4.98 (d. J=4Hz. 1H); IR (KBr): 1770 cm$^{-1}$.

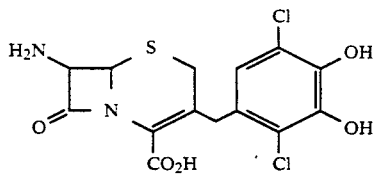

EXAMPLE 2

7-[2-(2-Aminothiazol-4-yl)-2-(syn)-(1-tert-butoxycarbonyl-1-methylethoxyimino)acetamido]-3-(2,5-dichloro-3,4-dihydroxyphenyl)methyl-3-cephem-4-carboxylic acid.

Title product of Example 1 (1.5 g) was dissolved in N, N-dimethylacetamide (DMAc). This solution was cooled to 0°~5° C. and mercaptobenzothiazol-2-(2-aminothiazol-4-yl)2-(1-tert-butoxycarbonyl-1-methyl ethoxyimino) acetate (2.01 g) was added to this solution. After stirring at 0°~5° C. for 30 minutes and at room temperature for 3 hours, the solution was poured into the mixture of ethylacetate (50 ml), methyl-acetate (50 ml) and water (50 ml). The organic layer was collected and water (30 ml) was added to the combined organic layer and the pH was adjusted to 6.5 with sodium bicarbonate. The resulting organic layer was dried up under reduced pressure. This residue was triturated in ether (20 ml), filtered off and dried in vacuo to give the title compound (1.01 g): NMR (DMSO-$d_6$) 1.38 (s, 9H), 1.39 (s, 3H), 1.42 (s, 3H), 3.0~4.3 (m,), 5.09(d. J=5Hz, 1H), 5.75(dd. J=5Hz, 8Hz, 1H), 6.70 (s.1H), 6.90 (s, 1H), 7.25 (bs, 2H), 9.32 (d, J=8Hz, 1H); IR (KBr): 1,770 cm$^{-1}$, 1,680 cm$^{-1}$,1,630 cm$^{-1}$.

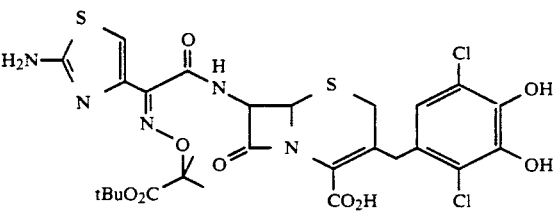

EXAMPLE 3

7-[2-(2-Aminothiazol-4-yl)-2-(syn)-1-carboxy-1-methylethoxyimino)acetamido)
3-(2,5-dichloro-3,4-dihydroxyphenyl)methyl-3-cephem-4-carboxylic acid Title product of Example 2 (1000 mg) was dissolved in trifluoroacetic acid (10 ml). After stirring at room temperature for 90 minutes, this solution was dried under reduced pressure. The residue was triturated in water, filtered and dried in vacuo. The resulting solids were purified by HPLC to give the title product (.00 mg): NMR (DMSO) 1.41 (S. 3H), 1.43 (S. 3H), 3.0~4.2 (m), 5.09 (d. J=5Hz, 1H), 5.76 (dd. J=5Hz, 1H), 6.72 (S. 1H), 6.86 (S. 1H), 7.28 bs. 2H), 9.34 (d. J=8Hz 1H); IR (KPr): 1,760 1,670 cm$^{-1}$, 1,630 cm$^{-1}$.

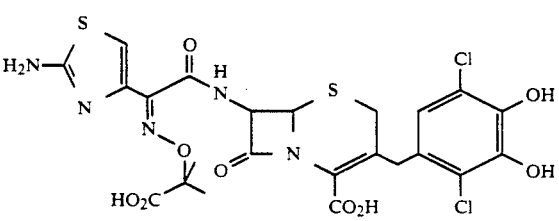

EXAMPLE 4-A

A—7-(2-(2-aminothiazol-4-yl)-2-(syn]-(1-Carboxy-1-methoxyimino)acetamido)
3-(6-bromo-3,4-dihydroxyphenyl)methyl-3-cephem-4-carboxylic acid B—7-(2-(2-aminothiazol-4-yl)-2-(syn)-(1-carboxy-1-methoxyimino)acetamide)
3-(dibromo-3,4-dihydroxyphyenyl)methyl-3-cephem-4-carboxylic acid To a solution of 7- (2-(2-aminothiazol-4-yl)-2-syn-(1-carboxy- 1-methoxyimino)acetamido)-3-(3,4-dihydroxyphenyl)methyl-3-cephem-4-carboxylic acid (2.0 g) in a mixture of dichloromethane (50 ml) and methyl alcohol (20 ml) was added benzyltrimethylammonium tr.bromide (1.74 g). After stirring at 5 to 10 ° C. for one hour, the resulting solution was poured into a solution of sodium hydrogen carbonate and stirred at 5 to 10° C for a half hour. The resulting solid was filtered off, and dried in vacuo. The sold was purified by high performance liquid chromatography (HPLC) to give the title produc-s of A(140 mg): and B (18 mg)

A—IR (KBr): 3,350, 1,760, 1,670, 1,530, 1,470, 1,360 (cml) NMR (DMSO-d$_6$) 1.42 (S, 3H), 1.44 (S, 3H), 3.14–3.43 (m), 3.68 and 3.76 (AB, J=5Hz, 2H), 5.16 (d, J=5Hz, 1H), 5.81 (dd, J=5Hz, 8Hz, 1H), 6.72 (S, 1H), 6.76 (S, 1H), 6.9 (S, 1H) 7.28 (bs, 2H), 9.40 (d, J=8Hz, 1H)

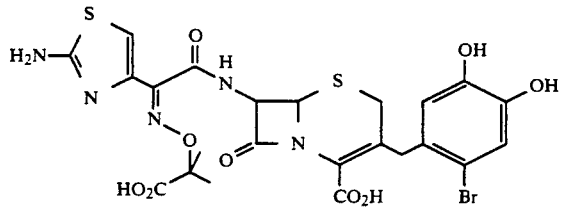

B—IR 1660, 1,510, 1,480, 1,360 (cml) NMR (DMSO)-d$_6$): 1.44 (S, 3H), 1.48 (S, 3H), 3.10-3.50 (m), 370 (bs, 2H), 5.13 (d, J=5z, 1H), 5.79 (dd, J=5Hz, 8Hz, 1H), 6.77 (S, 1H), 6.91 (S, 1H), 7.42 (bs,2H)

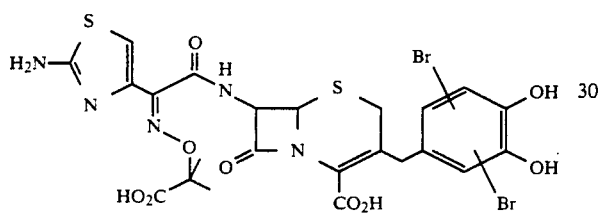

EXAMPLE 5

7-amino-3-(2,5-difluoro-3,4-dihydroxyphenyl)methyl-3-cephem-4-carboxylic acid

To a solution of 3,6-difluorocatechol (0.54 g) in a mixture of trifluoroacetic acid (TFA) (4.0 ml) and boron trifluoride etherate (4.0 ml) was added 7-aminocepharosporanic acid (1.0 g). After being stirred at 5° to 10° C. for one hour, the resulting solution was concentrated to a solid, which was washed with isopropyl ether and dried in vacuo to give the title product as TFA salt (1.67 g).

IR (KBr): 1,780 (cm$^{-1}$)

NMR (DMSOd$_6$) 3.20–3.90 (m), 5.12 (d, J=5Hz, 1H), 5.21 (d, J=5Hz, 1H), 6.54 (dd, J=6Hz, 12Hz, 1H)

EXAMPLE 6

7-(2-(2-aminothiazol-4-yl)-2-(syn)-(1-tert-butoxycarbonyl-1-methyletoxyimino)acetamido)-3-(2,5-difluoro-3,4-dihydroxyphenyl)methyl-3-cephem-4-carboxylic acid Title product of Example 5 (165 g) was treated with mercaptobenzothiazol-2-(2-aminothiazol-4-yl)-2-(1-tert-butoxycarbonyl-1-methylethoxyimino)acetate (2.42 g) in N, N-dimethylacetamido (DMAc) (5.0 ml) at room temperature for four hours. The resulting solution was diluted with ethyl acetate (10 ml) and water (10 ml. The organic layer was separated and washed with water four times. The ethyl acetate solution was concentrated to a residue, which was triturated in ether, filtered off and dried in vacuo to give the title product (2.22 g).

IR (KBr): 3,350, 1,780, 1,720, 1,680, 1,620, 1,530, 1,470, 1,360, 1,300 (cm$^{-1}$)

NMR (DMSO-d$_6$): 1,38 (S, 9H), 1.39 (S, 3H), 1.42 (S, 3H), 3.20-3.90 (m), 5.16 (d, J=5Hz, 1H), 5.80 (dd, J=5Hz, 8Hz, 1H), 6.53 (dd, J=6Hz, 11Hz, 1H), 6.70 (S, 1H), 7.26 (bs, 2H), 9.34 (d, J=8Hz, 1H)

EXAMPLE 7

7-(2-(2-aminothiazol-4-yl)-2-(syn)-(1-carboxy-1-methylethoxyimino)acetamido) -3-(2,5-difluoro-3,4-dihydroxyphenyl)methyl-3-cephem-4-carboxylic acid The title product of Example 6 (2.22 g) was dissolved in trifluoroacetic acid (10 ml) After stirring at room temperature for three hours, the resulting solution was concentrated. The residue was triturated in isopropyl ether, filtered off and dried in vacuo. The solid was purified by high performance liquid chromatography (HPLC) to give the title product (256.5 mg).

IR (KBR) 3,350, 1,770, 1,670, 1,520, 1,470, 1,360 (cm$^{-1}$)

NMR (DMSO-d$_6$): 3.17–3.99 (m), 5.17 (d, J=4Hz, 1H), 5.79 (dd, J 5Hz 9Hz, 1H), 6.52 (dd, J=6Hz, 11Hz, 1H), 6.71 (S, 1H), 7.31 (bs, 2H), 9.41 (d, J=9Hz, 1H)

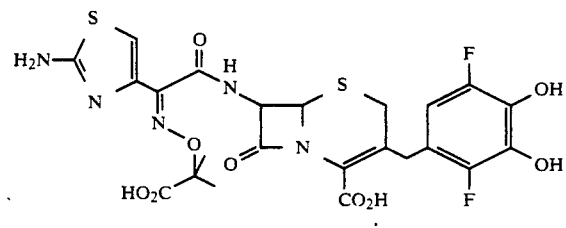

EXAMPLE 8

A. 7-amino-3-(2-fluoro-3,4-dihydroxyphenyl) methyl-3-cephem-4-carboxylic acid

B. 7-amino-3-(3-fluoro-4,5-dihydroxyphenyl) methyl-3-cephem-4-carboxylic acid 3-fluorocatechol 1.0 g was dissolved in 15% borontrifluoride acetonitrile solution. To the solution was added 7-aminocephalosporanic acid at 5° C. After the stirring for 40 hours at room temperature, the reaction mixture was concentrated to dryness and dissolved in water with the addition of sodium bicarbonate pH 7.0). The solution was washed with ethyl acetate and acidified with 6N-hydrochloric acid to pH The resulting crude crystals were collected by filtration and washed with water to give a mixture of the title compounds (1.74 g). The isolation and purification by high performance liquid chromatography (eluent; 3% acetonitrile in potassium phosphate buffer pH 6.0, column; ODS) gave the fractions of A and B as the order of elution. Each fraction was concentrated to dryness and the resulting solids were slurried in N,N-dimethylacetamide and filtered, respectively. Each DMAc solutions of title compounds A and B were submitted to the next step (Exp. 9 and Exp. 10) without further purification.

EXAMPLE 9

7-(2-(2-aminothiazol-4-yl)-2-(syn)-(1-t-butoxycarbonyl-1-methylethoxy-imino)acetamido)-3-(2-fluoro-3,4-dihydroxyphenyl)methyl-3-cephem-4-carboxylic acid To a DMAc solution of 7-amino-3-(2-fluoro-3,4-dihydroxyphenyl)methyl-3-cephem-4-carboxylic acid prepared in example 8 was added mercaptbenzothiazol-2-(2-aminothiazole-4-yl)-2-(1-t-butoxycarbonyl-1-methylethoxyimino)acetate(330 mg) and stirred for 20 hours at room temperature. The reaction mixture was concentrated to dryness and dissolved in a mixture of water and ethyl acetate. The organic layer was separated and extracted with water at pH 7.0 with the addition of sodium bicarbonate. Then the water layer wus washed with ethyl acetate, ethyl acetate was added and acidified with 6N-hydrochloric acid to pH 3.2. The ethyl acetate layer was concentrated to give the title compound 500 mg). NMR (DMSO-$d_6$), $\sigma$=1.38 (s, 9H), 1.40 (s, 3H), 1.42 (s, 3H) 3~4 (m, 4H), 5.15 (d, J=4Hz, 1H), 5.76 (dd, J=8, 4Hz, 1H), 6.52 (brs, 2H), 6.71 (s, 1H), 7.30 (brs, 2H), 8.96 (brs, 1H), 9.34 (d, J=8Hz, 1H), 9.34 (brs, 1H).

EXAMPLE 10

7-(2-(2-aminothiazol-4-yl)-2-(syn)-(1-t-butoxycarbonyl-1-methylethoxyimino)acetamido)-3-(3-fluoro-4,5-dihydroxyphenyl)methyl-3-cephem-4-carboxylic acid By the same procedure of example 9, 7-amino-3-(3-fluoro-4,5-dihydroxyphenyl)methyl-3-cephem-4-carboxylic acid prepared in example 8 was reacted with mercaptobenzothiazol-2-(2-aminothiazol-4-yl)-2-(1-t-butoxycarbonyl-1-methylethoxyimino)acetate 170 mg to give the title compound (50mg)

NMR (DMSO-$d_6$) $\sigma$=1.37 (s, 9H), 1.39 (s, 3H), 1.40 (s, 3H), 3.0~4.0 (m, 4H), 5.17 (d, J=4Hz 1H), 5.79 (dd, J=9, 4Hz, 1H), 6.4~6.6 (m, 2H), 6.70 (s, 1H), 7.24 (brs, 2H), 8.88 (brs, 1H), 9.33 (d, J=9Hz, 1H), 9.42 (brs, 1H)

EXAMPLE 11

7-(2-(2-aminothiazol-4-yl)-2-(syn)-(1-t-carboxyl-1-methylethoxyimino)acetamido)-3-(2-fluoro-3,4-dihydroxyphenyl)methyl-3-cephem-4-carboxylic acid 7-(2-(2-aminothiazol-4-yl)-2-(syn)-(1-t-butoxycarbonyl-1-methylethoxyimino)acetamido) -3-(2-fluoro-3,4-dihydroxyphenyl) methyl-3-cephem-4-carboxylic acid (500 mg) was dissolved in trifluoro acetic acid (2 ml) and stirred for 16 hours at room temperature. The reaction mixture was concentrated to dryness, 10ml of water was added and dissolved with the addition of sodium bicarbonate to pH 7.0. The solution was washed with ethyl acetate and the pH was adjusted to 3.2 with 6N-hydrochloric acid to give a crystal slurry. The crystals were collected by filtration, washed with water and dried to give the title compound(267 mg). IR (KBr) 1760, 1670, 1630 cm$^{-1}$ NMR (DMSO-$d_6$) $\sigma$=1.42 (s, 3H), 1.43 (s, 3H), 3~4.0 (m, 4H), 5.15 (d, J=4Hz, 1H) 5.77 (dd, J=8, 4Hz, 1H), 6.52 (brs, 2H), 6.72 (s, 1H), 7.28 (brs, 2H), 8.96 (brs, 1H), 9.31 (brs, 1H), 9.37 (d, J=8Hz, 1H)

EXAMPLE 12

7-(2-(2-aminothiazol-4-yl)-2-(syn)-(1-carboxy-1-methylethoxyimino)acetamido)-3-(3-fluoro-4,5-dihydroxyphenyl) methyl=3=cephem-4-carboxylic acid By the same process of example 11, 7-(2-(2-aminothiazol-4-yl)-2-(sny)-(1-t-butoxycarbonyl-1-methylethoxyimino) acetamido )-3-(3-fluoro-4,5-dihydroxyphenyl) methyl-3-cephem-4-carboxyl acid (50 mg) was treated with trifluoroacetic acid to give the title compound (29.4 mg).

IR (KBr) 1760, 1670, 1630 cm$^{-1}$

NMR (DMSO-$d_6$) $\sigma$=1.41 (s, 3H), 1.42 (s, 3H), 3.1~3.9 (m, 4H), 5.17 (d,J=4Hz, 1H), 5.77 (dd, J=8, 4Hz, 1H), 6.4~6.6 (m, 2H), 6.71 (s, 1H), 7.27 (brs, 2H), 8.87 (brs, 1H), 9.39 (d, J=8Hz, 1H), 9.43 (brs, 1H)

EXAMPLE 13

7-amino-3-(2-nitoro-3-,4-dihydroxyphenyl) methyl-3-cephem-4-carboxylic acid 3-nitroocatehol (2.1 g) and 7-amino-3-cephem-4-carboxylic acid (2.5 g) were dissolved in 15% boron trifluoride acetonitrile solution (17.1 ml). After stirring at 0°~5° C. for 4 hours, the reaction mixture was diluted with water (80 ml). The solution was adjusted to pH 3.5 with ammonium water and the resulting solids were filtered, washed with water and dried in vacuo. The solids were dissolved into water (57 ml) by adjusting to pH 0.8 with 6N hydrochloric acid. After carbon treatment, the solution was adjusted to pH 3.5 with ammonium water. The resulting solids were filte ed off, washed with water and dried in vacuo to give the title compound (1.09 g).

IR (KBr) 1770 c$^{-1}$

NMR (DMSO-$d_6$): 3.08 and 3.36 (ABm J=18Hz, 2H), 3.51 and 3.61 (AB, J=15Hz, 2H), 4.77 (d. J=5Hz, 1H). 6.62 (d, J=8Hz, 1H), 6.90 (d, J=8Hz, 1H)

EXAMPLE 14

7-(2-(2-aminothiazol-4-yl)-2-(syn)-(1-tert-butoxycarbonyl-1-methylethoxyimino)acetamido)-3-(2-nitro-2,4-dihydroxyphenyl) methyl-3-cephem-4-carboxylic acid Title product of example 13 (1 g) and mercaptobezothiazol-2-(2-aminothiazol-4-yl)-2-(l-t-butoxycarbonyl-1-methylethoxyimino)acetate (1.63 g) were dissolved in N,N-dimethylacetoamide (4 ml) and the solution was stirred at room temperature for 2.5 hours. This solution was poured into the mixture of ethylacetate (16 ml) and water (16 ml). The organic layer was separated, washed with water and extracted into water layer with aq. NaHCO$_3$ at pH 6.5. The seperated aqueous layer was washed with ethylacetate (10 ml) and diluted with water (20 ml). The solution was adjusted to pH 2.5, and the resulting solids were filtered off, washed with water and dried in vacuo to give the title compound (1.42 g).

IR (KBr) 3,350cm$^{-1}$, 1,770 cm$^{-1}$, 1,670cm$^{-1}$, 1,630cm NMR (DMSO-$d_6$1.38: (s, 9H), 1.4 (s, 3H), 1.42 (s, 3H), 3.1~3.5(m),3.55~3.68(AB,J=15Hz,2H),5.13(d,J=4Hz,1H), 5.80(dd,J=4Hz,8Hz, 1H), 6.62 (d, J=8Hz, 1H), 6.71 (s, 1H), 6.89 (d, J=8Hz, 1H), 7.26 (bs, 1H), 9.34 (d, J=8Hz, 1H), 9.89 (bs, 1H), 10.16 (bs, 1H)

EXAMPLE 15

7-(2-(2-aminothiazol-4-yl)-2-(sny)-(1-carboxy-1-methlethoxyimino)acetamido)
-3-(2-nitro-3,4-dihydroxyphenyl) dihydroxyphenyl) methyl-3-cephem-4-carboxylio acid.

Title product of example 14 (0.759, was dissolved in trifluoroacetic acid (3.75 ml). After stirring at room temperature for 2 hours the solution was concentrated to a solid, which was washed with iscpropylether (7.5 ml) and dried in vacuo. The resulting solids were dissolved in a mixture of water (7.2 ml) and ethylacetate (3.6 ml) and dissolved by adjusting the pH to 4.5 with sodium bicarbonate. The aqueous layers were washed with ethylacetate (3.6 ml) and diluted with water (7.2 ml). After stirring at 10° C, the solution was adjusted to pH 2.5 with 6NHCl. The resulting solids were filteted off, washed with water and dried in vacuo to give the title compound (0.54 g).

IR (KBr) 3,350cm$^{-1}$, 1,770cm$^{-1}$, 1,670cm$^{-1}$, 1,630cm$^{-1}$,

NMR (CMSO-d$_6$) 1.42 (s, 3H), 1.43 (s, 3H), 3.1~3.5 (m), 3.60 (s, 2H), 5.14 (d, J=5Hz, 1H), 5.81 (dd, J=5Hz, 8Hz, 1H), 6.623(d, J=8Hz, 1H), 6.72 (s, 1H), 6.89 (d, J=8Hz, 1H), 7.30 (bs, 2H), 9.42 (d, J=8Hz, 1H), 9.91 (bs, 1H), 10.18 (bs, 1H)

EXAMPLE 16

7-(2-(2-aminothiazol-4-yl)-2-(syn)-(I-tert-butoxycarbonyl-1-methylethoxyimino)acetamido)-3-(2,5-difluoro-3,4-dihydroxyphenyl) methyl-3-cephem-4-carboxylic acid HCl salt The title product of example 6 (4.38 g) was dissolved in ethanol (35ml). To the solution was added 6NHCI (35 ml) and the resulting solution was sti-red on an ice bath to give a crystalline slurry. The crystals were filtered off, washed with a mixture of ethanol and water (1:2) and then with water, and dried in vacuo at 40 ° C. to give 3.09 g of the title product.

IR (KBr),1,767, 1,714, 1,704, 1,669, 1,630, 1,370, 1,303, 1,148 (cm$^{-1}$)

NMR (DMSO-d$_6$) 1.38 (s, 9H), 1.45 (s, 3H), I.47 (s, 1H), 3.20~3.83 (m), 5.18 (d, J-5Hz, 1H), 5.78(dd, J=5Hz, 8Hz, 1H), 6.51 (dd, J=7Hz, 11Hz, 1H), 6.88 (s, 1H , 9.51 (d, J=8Hz, 1H)

I claim:

1. A compound of the formula

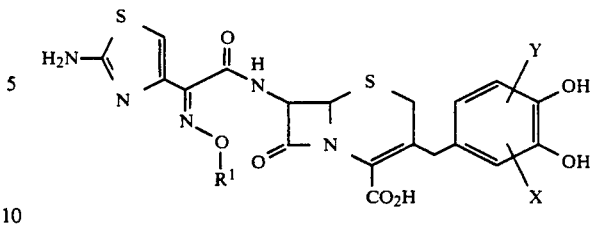

or a pharmaceutically-acceptable salt or in vivo hydrolysable ester thereof wherein R$^1$ is lower alkyl substituted by a carboxyl, cyano, halo, hydroxyl or protected carboxyl group; and X is hydrogen or halo and Y is halo.

2. A compound according to claim 1 wherein R$^1$ is selected from:

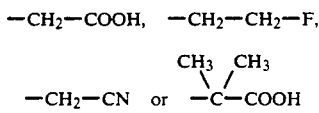

3. A compound according to claim 2 wherein X and Y are selected from: 2,5-difluoro, 2,5-dichloro, 2,6-dibromo, 2-fluoro or 5-fluoro.

4. A compound according to claim 3, said compound being 7-[2-(2-amninothiazol-4-yl)-2-syn-(1-carboxy-1-methylethoxyimino)acetamido]-3-(2,5-difluoro-3,4-dihydroxyphenyl)methyl-3-cephem-4-carboxylic acid.

5. A compound according to claim 3, said compound being 7-[2(2-aminothiazol-4-yl)-2-syn-(1-carboxy-1-methylethoxyimino)acetamido]-3-(2,5-dichloro-3,4-dihydroxyphenyl)methyl-3-cephem-4-carboxylic acid.

6. A compound according to claim 3, said compound being 7-[2-(2-aminothiazol-4-yl)-2-syn-(1-carboxy-1-methylethoxyimino)acetamido]-3-(2,6-dibromo-3,4-dihydroxyphenyl)methyl-3-cephem-4-carboxylic acid.

7. A compound according to claim 3, said compound being 7-[2-(2-aminothiazol-4-yl)-2-syn-(1-carboxy-1-methylethoxyimino)acetamido[-3-(2-fluoro-3,4-dihydroxyphenyl)methyl-3-cephem-4-carboxylic acid.

8. A compound according to claim 3, said compound being 7-[2-(2-aminothiazol-4-yl)-2-syn-(1-carboxy-1-methylethoxyimino)acetamido]-3-(5-fluoro-3,4-dihydroxyphenyl)methyl-3-cephem-4-carboxylic acid.

9. A pharmaceutical composition for the treatment of a bacterial infection in a mammal which comprises a compound of claim 1 in a pharmaceutically-acceptable carrier or diluent.

10. A method of treating a bacterial infection which comprises administering to a mammal suffering from a bacterial infection an antibacterial effective amount of a compound of claim 1.

* * * * *